United States Patent [19]
Seilhamer et al.

[11] Patent Number: 5,756,333
[45] Date of Patent: May 26, 1998

[54] RECOMBINANT PRODUCTION OF LACTOPEROXIDASE

[75] Inventors: Jeffrey J. Seilhamer, Milpitas; Thomas J. Dull, San Francisco, both of Calif.

[73] Assignee: Incyte Pharmaceuticals, Inc., Palo Alto, Calif.

[21] Appl. No.: 273,368

[22] Filed: Jul. 11, 1994

Related U.S. Application Data

[63] Continuation of Ser. No. 928,933, Aug. 12, 1992, abandoned, which is a continuation-in-part of Ser. No. 431,634, Nov. 3, 1989, abandoned.

[51] Int. Cl.$^6$ .............................. C12N 9/08; C12Q 1/68; C12P 21/06; C07H 19/00
[52] U.S. Cl. .............................. 435/192; 435/6; 435/69.1; 435/252.3; 435/320.1; 435/22.1; 435/23.1; 435/23.2; 435/23.5
[58] Field of Search .............................. 435/6, 69.1, 192, 435/252.3, 320.1; 536/22.1, 23.1, 23.2, 23.5

[56] References Cited

U.S. PATENT DOCUMENTS 4,576,817  3/1986  Montgomery et al. ................. 424/94.1

FOREIGN PATENT DOCUMENTS

| | | |
|---|---|---|
| 2613725 | 10/1988 | France . |
| 2162063 | 1/1986 | United Kingdom . |
| WO 89/04608 | 6/1989 | WIPO . |

OTHER PUBLICATIONS

Mailliart, Pascal, Ph.D. Thesis Abstract entitled "Contribution to the valorization of bovine whey proteins: from purification to sequence analysis," University of Paris, (1989) 1 page total.

Kimura et al., "Human thyroid peroxidase: Complete cDNA and protein sequence, chromosome mapping, and identification of two alternately spliced mRNAs," *Proc. Natl. Acad. Sci.* (1987) 84:5555–5559.

Kimura et al, "cDNA–directed expression of human thyroid peroxidase," *FEBS Letters* (1989) 250(2):377–380.

Langbakk et al., "Lactoperoxidase from human colostrum," *Biochem. J.* (1989) 259:627–631.

Sievers, "Structure of Milk Lactoperoxidase: Evidence for a single polypeptide chain," *FEBS Letters* (1981) 127(2):253–256.

Glover, "The Principles of Cloning DNA," *Gene Cloning*, Chapman and Hall, New York, 1984, pp. 1–19.

Goff et al., "High Resolution Proton Nuclear Magnetic Resonance Spectroscopy of Lactoperoxidase," *Biochem. Biophys. Res. Comm.* (1985) 133:(2) 794–799.

Booth et al., "Bovine Myeloperoxidase and Lactoperoxidase Each Contain a High Affinity Site for Calcium," *Biochem. Biophys. Res. Comm.* (1989) 160(2) 897–902.

Carlström, "Physical and Compositional Investigations of the Subfractions of Lactoperoxidase," *ACTA Chem. Scand.* (1969) 23(1):185–202.

Paul et al., "The Chemical Structure of Lactoperoxidase," *Immunol. Ser.* (1983) 27:15–29.

Langbakk et al., "Demonstration and partial purification of lactoperoxidase from human colostrum," *FEBS Letters* (1984) 174(2):300–303.

Suggs et al., "Use of synthetic oligonucleotides as hybridization probes," *Proc. Natl. Acad. Sci.* (1981) 78(11) 6613–6616.

Carlström, "Lactoperoxidase: Some Spectral Properties of a Haemoprotein with a Prosthetic Group of Unknown Structure," *ACTA Chem. Scand.* (1969) 23:203–213.

Shindler et al., "Peroxidase from Human Cervical Mucus," *Eur. J. Biochem.* (1976) 65:325–331.

Tenovuo, "Different Molecular Forms of Human Salivary Lactoperoxidase," *Archs. Oral Biol.* (1981) 26:1051–1055.

Carlsson et al., "Hydrogen Peroxide Excretion by Oral Streptococci and Effect of Lactoperoxidase–Thiocyanate–Hydrogen Peroxide," *Infect. & Immun.* (1983) 40(1):70–80.

Carlström, "Lactoperoxidase: Identification of Multiple Molecular Forms and their Interrelationships," *ACTA Chem. Scand.* (1969) 23:171–184.

Ericsson et al., "Endogenous antibodies to bovine lactoperoxidase in children and adolescents," *Allergy* (1987) 42:430–433.

Gothefors et al., "Lactoperoxidase Activity in Human Milk and in Saliva of Newborn Infants," *Infect. & Immun.* (1975) 11(6):1210–1215.

Pfeil et al., "Lactoperoxidase consists of domains: a scanning calorimetric study," *Biochem. Biophys. Acta* (1986) 872:72–75.

Reiter et al., "An Evaluation of the Growth Promoting Effect of the Lactoperoxidase System in Newborn Calves," *Anim. Prod.* (1981) 32:297–306.

Rombauts et al., "Bovine Lactoperoxidase. Partial Characterization of the Further Purified Protein," *Biochemistry* (1967) 6(10):2965–2977.

Mailliart, Pascal On–Line Database, Ph.D. Thesis Abstract entitled "Contribution a la Valorisation des Proteines du Lactoserum de la Purification au Sequencage", University of Paris, (1989), 1 page total.

Kimura et al., *Proc. Natl. Acad. Sci.* (1987) 84:5555–5559.
Kimura et al., *FEBS Letters* (1989) 250(2):377–380.
Dull et al., *DNA and Cell Biology* (1990) 9(7):499–509.

(List continued on next page.)

*Primary Examiner*—Vasu S. Jagannathan
*Assistant Examiner*—Hyosuk Kim
*Attorney, Agent, or Firm*—Karl Bozicevic; Carol Francis; Fish & Richardson P.C.

[57] ABSTRACT

Recombinant methods and materials useful in producing lactoperoxidases are disclosed. An illustrative form of lactoperoxidase is the bovine protein shown in FIG. 1. FIG. 1 also shows the DNA sequence natively encoding the bovine lactoperoxidase, including contiguous regions of the gene. Such DNAs are useful in a variety of applications including antisense technology, formation of triple helices, and performance of diagnostic assays.

8 Claims, 13 Drawing Sheets

OTHER PUBLICATIONS

Sievers "Structure of Milk Lactoperoxidase" *FEBS Letters* May, 1981 pp. 253–256.

Langbakk "Lactoperoxidase From Human Colostrum." *Biochem J.* (1989) 259: 627–631.

Glover "Principles of DNA Cloning" *Gene Cloning* 1984 pp. 1–19.

Lee et al. "Generation of cDNA Probes . . . " *Science* 239:1288–1291 (1988).

Green et al "The Role of Antisense RNA . . . " *Ann Rev. Biochem.* 1986 55:569–97.

Goff et al., *Biochem. Biophys. Res. Comm.* (1985) 133(2):794–799.

Langbakk et al., *Biochem. J.* (1989) 259:627–631.

Booth et al., *Biochem. Biophys. Res. Comm.* (1989) 160(2):897–902.

Carlstrom, *ACTA Chem. Scand.* (1969) 23(1):185–202.

Sievers et al., *FEBS Letters* (1981) 127(2):253–256.

Paul et al., *Immunol. Ser.* (1983) 27:15–29.

Langbakk et al., *FEBS Letters* (1984) 174(2):300–303.

Suggs et al., *Proc. Natl. Acad. Sci.* (1981) 78(11):6613–6616.

Carlsson et al., *Infect & Immun.* (1983) 40(1):70–80.

Carlstrom et al., *ACTA Chem. Scand.* (1969) 23:171–184.

Calstrom et al., *ACTA Chem. Scand.* (1969) 23:203–213.

Ericsson et al., *Allergy* (1987) 42:430–433.

Gothefors et al., *Infect & Immun.* (1975) 11(6):1210–1215.

Pfeil et al., *Biochem. Biophys. Acta* (1986) pp. 72–75.

Reiter et al., *Anim. Prod.* (1981) 32:297–306.

Rombauts et al., *Biochemistry* (1967) 6(10):2965–2977.

Shindler et al., *Eur. J. Biochem.* (1976) 65:325–331.

Tenovuo, *Archs. Oral Biol.* (1981) 26:1051–1055.

Bovine Lactoperoxidase cDNA

| | | | | | | | | | |
|---|---|---|---|---|---|---|---|---|---|
| EcoRI-CA | GAA | TCT | TTC | CTT | CTG | GGC | TTT | TCT | 26 |
| 27 | CTG | AGA | TTA | ACT | CTT | GAT | AGA | CGG | TAT | 53 |
| 54 | AAA | AGG | CCG | GCT | CCT | CCA | AGC | AGA | GAA | 80 |
| 81 | ACT | CCC | TCT | GGC | TGC | CAC | AGG | AGG | CCA | 107 |
| 108 | AGG | CAC | TCA | ATA | GCG | ATG | TGG | GTC | TGT | 134 |
| 1 | | | | | | Met | Trp | Val | Cys | 4 |
| 135 | CTC | CAA | CTT | CCA | GTC | TTT | TTG | GCT | TCC | 161 |
| 5 | Leu | Gln | Leu | Pro | Val | Phe | Leu | Ala | Ser | 13 |
| 162 | GTG | ACC | TTA | TTC | GAG | GTT | GCA | GCA | TCT | 188 |
| 14 | Val | Thr | Leu | Phe | Glu | Val | Ala | Ala | Ser | 22 |
| 189 | GAC | ACA | ATT | GCA | CAG | GCC | GCC | AGC | ACC | 215 |
| 23 | Asp | Thr | Ile | Ala | Gln | Ala | Ala | Ser | Thr | 31 |
| | | | | | ^1 | ^2 | | | |
| 216 | ACC | ACC | ATC | TCT | GAT | GCT | GTG | AGT | AAG | 242 |
| 32 | Thr | Thr | Ile | Ser | Asp | Ala | Val | Ser | Lys | 40 |
| 243 | GTC | AAG | ATC | CAG | GTC | AAC | AAG | GCC | TTC | 269 |
| 41 | Val | Lys | Ile | Gln | Val | Asn | Lys | Ala | Phe | 49 |
| 270 | CTG | GAT | TCC | CGG | ACC | AGG | CTG | AAG | ACG | 296 |
| 50 | Leu | Asp | Ser | Arg | Thr | Arg | Leu | Lys | Thr | 58 |
| 297 | ACC | TTG | AGC | TCT | GAG | GCA | CCC | ACC | ACC | 323 |
| 59 | Thr | Leu | Ser | Ser | Glu | Ala | Pro | Thr | Thr | 67 |
| 324 | CAA | CAG | CTC | TCA | GAG | TAC | TTC | AAG | CAC | 350 |
| 68 | Gln | Gln | Leu | Ser | Glu | Tyr | Phe | Lys | His | 76 |
| 351 | GCA | AAG | GGC | CGG | ACC | CGC | ACG | GCC | ATT | 377 |
| 77 | Ala | Lys | Gly | Arg | Thr | Arg | Thr | Ala | Ile | 85 |
| 378 | CGC | AAC | GGG | CAG | GTG | TGG | GAG | GAG | TCC | 404 |
| 86 | Arg | Asn | Gly | Gln | Val | Trp | Glu | Glu | Ser | 94 |
| 405 | TTA | AAG | AGG | CTG | AGG | CGG | GAC | ACA | ACC | 431 |
| 95 | Leu | Lys | Arg | Leu | Arg | Arg | Asp | Thr | Thr | 103 |
| | | | | | | | ^B | | |

FIG. 1-1

```
432  CTG ACC AAC GTC ACA GAC CCT AGC CTG              458
104  Leu Thr Asn Val Thr Asp Pro Ser Leu              112

459  GAC TTG ACT GCA CTC TCC TGG GAG GTG              485
113  Asp Leu Thr Ala Leu Ser Trp Glu Val              121

486  GGC TGC GGT GCC CCG GTT CCT CTG GTG              512
122  Gly Cys Gly Ala Pro Val Pro Leu Val              130
                                     ^A^
513  AAA TGT GAT GAA AAC AGC CCT TAC CGC              539
131  Lys Cys Asp Glu Asn Ser Pro Tyr Arg              139

540  ACC ATC ACG GGA GAC TGT AAT AAC AGG              566
140  Thr Ile Thr Gly Asp Cys Asn Asn Arg              148

567  AGG AGC CCC GCA CTG GGC GCC GCC AAC              593
149  Arg Ser Pro Ala Leu Gly Ala Ala Asn              157

594  AGG GCG CTG GCG CGC TGG CTG CCG GCG              620
158  Arg Ala Leu Ala Arg Trp Leu Pro Ala              166

621  GAG TAC GAG GAC GGG CTC GCC CTG CCC              647
167  Glu Tyr Glu Asp Gly Leu Ala Leu Pro              175

648  TTC GGC TGG ACG CAG AGG AAG ACG CGC              674
176  Phe Gly Trp Thr Gln Arg Lys Thr Arg              184

675  AAC GGC TTC CGC GTC CCG CTG GCC CGG              701
185  Asn Gly Phe Arg Val Pro Leu Ala Arg              193

702  GAG GTA TCC AAC AAA ATT GTA GGC TAC              728
194  Glu Val Ser Asn Lys Ile Val Gly Tyr              202

729  CTG GAC GAA GAG GGT GTT CTG GAC CAA              755
203  Leu Asp Glu Glu Gly Val Leu Asp Gln              211

756  AAC AGG TCC CTG CTC TTC ATG CAG TGG              782
212  Asn Arg Ser Leu Leu Phe Met Gln Trp              220

783  GGT CAG ATT GTG GAC CAC GAC CTG GAC              809
221  Gly Gln Ile Val Asp His Asp Leu Asp              229

810  TTC GCC CCG GAA ACG GAA CTG GGG AGC              836
230  Phe Ala Pro Glu Thr Glu Leu Gly Ser              238

837  AAC GAG CAC TCT AAA ACC CAG TGT GAG              863
239  Asn Glu His Ser Lys Thr Gln Cys Glu              247
```

FIG. 1-2

| | | | | | | | | | |
|---|---|---|---|---|---|---|---|---|---|
| 864 | GAG | TAC | TGT | ATC | CAG | GGA | GAC | AAC | TGC | 890 |
| 248 | Glu | Tyr | Cys | Ile | Gln | Gly | Asp | Asn | Cys | 256 |
| 891 | TTC | CCC | ATC | ATG | TTC | CCG | AAA | AAT | GAT | 917 |
| 257 | Phe | Pro | Ile | Met | Phe | Pro | Lys | Asn | Asp | 265 |
| 918 | CCC | AAG | TTG | AAG | ACT | CAA | GGG | AAA | TGC | 944 |
| 266 | Pro | Lys | Leu | Lys | Thr | Gln | Gly | Lys | Cys | 274 |
| 945 | ATG | CCT | TTC | TTC | CGA | GCC | GGG | TTT | GTC | 971 |
| 275 | Met | Pro | Phe | Phe | Arg | Ala | Gly | Phe | Val | 283 |
| 972 | TGC | CCC | ACT | CCA | CCT | TAC | CAG | TCG | TTG | 998 |
| 284 | Cys | Pro | Thr | Pro | Pro | Tyr | Gln | Ser | Leu | 292 |
| 999 | GCC | CGA | GAA | CAG | ATC | AAT | GCT | GTG | ACC | 1025 |
| 293 | Ala | Arg | Glu | Gln | Ile | Asn | Ala | Val | Thr | 301 |
| 1026 | TCC | TTC | CTG | GAC | GCC | AGC | TTA | GTG | TAC | 1052 |
| 302 | Ser | Phe | Leu | Asp | Ala | Ser | Leu | Val | Tyr | 310 |
| 1053 | GGC | TCT | GAG | CCC | AGT | CTG | GCC | AGC | CGT | 1079 |
| 311 | Gly | Ser | Glu | Pro | Ser | Leu | Ala | Ser | Arg | 319 |
| 1080 | CTC | CGG | AAC | CTC | AGC | AGC | CCG | CTG | GGC | 1106 |
| 320 | Leu | Arg | Asn | Leu | Ser | Ser | Pro | Leu | Gly | 328 |
| 1107 | CTC | ATG | GCT | GTC | AAC | CAA | GAA | GCC | TGG | 1133 |
| 329 | Leu | Met | Ala | Val | Asn | Gln | Glu | Ala | Trp | 337 |
| 1134 | GAC | CAC | GGG | CTG | GCC | TAC | CTG | CCC | TTT | 1160 |
| 338 | Asp | His | Gly | Leu | Ala | Tyr | Leu | Pro | Phe | 346 |
| 1161 | AAC | AAC | AAG | AAG | CCG | AGC | CCC | TGT | GAG | 1187 |
| 347 | Asn | Asn | Lys | Lys | Pro | Ser | Pro | Cys | Glu | 355 |
| 1188 | TTC | ATC | AAC | ACC | ACC | GCC | CGC | GTG | CCC | 1214 |
| 356 | Phe | Ile | Asn | Thr | Thr | Ala | Arg | Val | Pro | 364 |
| 1215 | TGT | TTC | CTG | GCG | GGA | GAT | TTT | CGA | GCC | 1241 |
| 365 | Cys | Phe | Leu | Ala | Gly | Asp | Phe | Arg | Ala | 373 |
| 1242 | TCA | GAG | CAG | ATT | CTG | CTG | GCC | ACT | GCC | 1268 |
| 374 | Ser | Glu | Gln | Ile | Leu | Leu | Ala | Thr | Ala | 382 |
| 1269 | CAC | ACC | CTC | CTT | CTC | CGG | GAG | CAC | AAC | 1295 |
| 383 | His | Thr | Leu | Leu | Leu | Arg | Glu | His | Asn | 391 |

FIG. 1-3

```
1296  CGG CTG GCC AGA GAA CTA AAG AAA CTC  1322
 392  Arg Leu Ala Arg Glu Leu Lys Lys Leu   400

1323  AAC CCT CAC TGG AAT GGA GAG AAG CTC  1349
 401  Asn Pro His Trp Asn Gly Glu Lys Leu   409

1350  TAC CAG GAA GCC CGG AAA ATC CTG GGA  1376
 410  Tyr Gln Glu Ala Arg Lys Ile Leu Gly   418

1377  GCC TTC ATA CAG ATC ATC ACC TTT AGG  1403
 419  Ala Phe Ile Gln Ile Ile Thr Phe Arg   427

1404  GAC TAC CTA CCC ATT GTG CTA GGT AGT  1430
 428  Asp Tyr Leu Pro Ile Val Leu Gly Ser   436

1431  GAG ATG CAG AAG TGG ATC CCG CCC TAC  1457
 437  Glu Met Gln Lys Trp Ile Pro Pro Tyr   445

1458  CAA GGC TAT AAT AAC TCT GTG GAT CCC  1484
 446  Gln Gly Tyr Asn Asn Ser Val Asp Pro   454

1485  CGA ATT TCC AAT GTC TTC ACC TTT GCC  1511
 455  Arg Ile Ser Asn Val Phe Thr Phe Ala   463

1512  TTC CGC TTT GGC CAC ATG GAG GTT CCC  1538
 464  Phe Arg Phe Gly His Met Glu Val Pro   472

1539  TCC ACT GTG TCC CGC CTG GAT GAG AAT  1565
 473  Ser Thr Val Ser Arg Leu Asp Glu Asn   481

1566  TAC CAG CCA TGG GGT CCG GAA GCA GAG  1592
 482  Tyr Gln Pro Trp Gly Pro Glu Ala Glu   490

1593  CTC CCC CTA CAC ACC CTC TTC TTC AAC  1619
 491  Leu Pro Leu His Thr Leu Phe Phe Asn   499

1620  ACC TGG AGG ATA ATC AAA GAC GGT GGA  1646
 500  Thr Trp Arg Ile Ile Lys Asp Gly Gly   508

1647  ATT GAC CCT CTG GTG CGG GGT CTG CTG  1673
 509  Ile Asp Pro Leu Val Arg Gly Leu Leu   517

1674  GCC AAG AAG TCC AAA CTG ATG AAT CAG  1700
 518  Ala Lys Lys Ser Lys Leu Met Asn Gln   526

1701  GAT AAA ATG GTG ACG AGT GAG CTG CGC  1727
 527  Asp Lys Met Val Thr Ser Glu Leu Arg   535
```

FIG. 1-4

| | | | | | | | | | |
|---|---|---|---|---|---|---|---|---|---|
| 1728 | AAC | AAG | CTT | TTC | CAG | CCC | ACT | CAC | AAG | 1754 |
| 536 | Asn | Lys | Leu | Phe | Gln | Pro | Thr | His | Lys | 544 |
| 1755 | ATC | CAC | GGC | TTT | GAC | CTG | GCT | GCT | ATC | 1781 |
| 545 | Ile | His | Gly | Phe | Asp | Leu | Ala | Ala | Ile | 553 |
| 1782 | AAC | TTA | CAG | CGT | TGC | CGA | GAC | CAT | GGG | 1808 |
| 554 | Asn | Leu | Gln | Arg | Cys | Arg | Asp | His | Gly | 562 |
| 1809 | ATG | CCT | GGG | TAC | AAC | TCC | TGG | AGG | GGC | 1835 |
| 563 | Met | Pro | Gly | Tyr | Asn | Ser | Trp | Arg | Gly | 571 |
| 1836 | TTC | TGT | GGC | CTC | TCA | CAG | CCC | AAG | ACA | 1862 |
| 572 | Phe | Cys | Gly | Leu | Ser | Gln | Pro | Lys | Thr | 580 |
| 1863 | CTG | AAG | GGG | CTG | CAG | ACT | GTG | CTG | AAG | 1889 |
| 581 | Leu | Lys | Gly | Leu | Gln | Thr | Val | Leu | Lys | 589 |
| 1890 | AAC | AAG | ATA | CTG | GCT | AAG | AAG | TTA | ATG | 1916 |
| 590 | Asn | Lys | Ile | Leu | Ala | Lys | Lys | Leu | Met | 598 |
| 1917 | GAT | CTC | TAT | AAG | ACC | CCC | GAC | AAC | ATT | 1943 |
| 599 | Asp | Leu | Tyr | Lys | Thr | Pro | Asp | Asn | Ile | 607 |
| 1944 | GAC | ATC | TGG | ATT | GGA | GGC | AAC | GCT | GAG | 1970 |
| 608 | Asp | Ile | Trp | Ile | Gly | Gly | Asn | Ala | Glu | 616 |
| 1971 | CCC | ATG | GTA | GAA | AGG | GGC | CGG | GTG | GGG | 1997 |
| 617 | Pro | Met | Val | Glu | Arg | Gly | Arg | Val | Gly | 625 |
| 1998 | CCA | CTC | CTG | GCC | TGC | CTC | CTA | GGG | AGG | 2024 |
| 626 | Pro | Leu | Leu | Ala | Cys | Leu | Leu | Gly | Arg | 634 |
| 2025 | CAA | TTC | CAG | CAG | ATA | CGT | GAT | GGG | GAC | 2051 |
| 635 | Gln | Phe | Gln | Gln | Ile | Arg | Asp | Gly | Asp | 643 |
| 2052 | AGG | TTC | TGG | TGG | GAG | AAC | CCT | GGG | GTC | 2078 |
| 644 | Arg | Phe | Trp | Trp | Glu | Asn | Pro | Gly | Val | 652 |
| 2079 | TTC | ACT | GAG | AAG | CAG | CGG | GAC | TCT | CTA | 2105 |
| 653 | Phe | Thr | Glu | Lys | Gln | Arg | Asp | Ser | Leu | 661 |
| 2106 | CAG | AAA | GTG | TCC | TTC | TCA | CGC | CTC | ATC | 2132 |
| 662 | Gln | Lys | Val | Ser | Phe | Ser | Arg | Leu | Ile | 670 |
| 2133 | TGT | GAC | AAC | ACC | CAC | ATC | ACG | AAG | GTC | 2159 |
| 671 | Cys | Asp | Asn | Thr | His | Ile | Thr | Lys | Val | 679 |

FIG. 1-5

| | | | | | | | | | |
|---|---|---|---|---|---|---|---|---|---|
| 2160 | CCG | CTG | CAT | GCC | TTC | CAG | GCC | AAC | AAC | 2186 |
| 680 | Pro | Leu | His | Ala | Phe | Gln | Ala | Asn | Asn | 688 |
| 2187 | TAC | CCA | CAT | GAC | TTT | GTG | GAT | TGC | TCA | 2213 |
| 689 | Tyr | Pro | His | Asp | Phe | Val | Asp | Cys | Ser | 697 |
| 2214 | ACC | GTT | GAT | AAG | CTG | GAT | CTC | TCA | CCC | 2240 |
| 698 | Thr | Val | Asp | Lys | Leu | Asp | Leu | Ser | Pro | 706 |
| 2241 | TGG | GCC | TCC | AGG | GAG | AAT | TAG | GGG | CCC | 2267 |
| 707 | Trp | Ala | Ser | Arg | Glu | Asn | | | | 712 |
| 2268 | GGA | CTC | CAC | AGC | CTC | CCA | CAC | TGT | GCA | 2294 |
| 2295 | GTA | GAG | CTC | CCC | TTG | GCC | ACG | ATG | CCA | 2321 |
| 2322 | TTT | CAA | GTA | GAC | TCA | GTG | ACC | TGG | CCC | 2348 |
| 2349 | CTT | CGG | GCT | CCC | TAC | CCC | GCC | CCA | GGC | 2375 |
| 2376 | CTT | CTG | TCC | AGC | CGA | GTC | TCT | CTG | CAC | 2402 |
| 2403 | GCC | CCC | CAA | GCA | CAC | CTA | GCT | CAA | GCC | 2429 |
| 2430 | CAA | GGC | AGC | CGC | CTT | GCC | GCT | CCA | GCT | 2456 |
| 2457 | CTT | CCC | ATT | GAA | TCC | CAC | ATC | CTC | TCC | 2483 |
| 2484 | GTC | TTC | GGA | AAC | CCT | CCT | TCT | GTC | AAG | 2510 |
| 2511 | ACT | TAC | ACC | CTC | CAA | AAT | GCC | TTC | TGA | 2537 |
| 2538 | TCT | TGC | TTG | CCA | GAT | GTC | ACC | CAT | CCT | 2564 |
| 2565 | TTC | CCC | AAA | AAA | AGT | CTT | GGC | TGA | GGC | 2591 |
| 2592 | TGT | GGC | CTT | GAC | ACC | TGT | ATC | TCT | CCT | 2618 |
| 2619 | CCC | CTT | GAA | CTA | GAT | TGT | AAA | CTT | CTT | 2645 |
| 2646 | GAG | CTT | GGC | CTT | CAA | CCT | GCT | TCC | AAG | 2672 |
| 2673 | TGT | GCC | CTG | GGG | CCC | CCA | GCG | TAG | TCC | 2699 |
| 2700 | TTG | GCA | CAC | AG-EcoRI | | | | | | 2710 |

(EcoRI = cloning linker)

Human Lactoperoxidase (partial)

| | | | | | | | | | |
|---|---|---|---|---|---|---|---|---|---|
| 1 | G | GAG | CAT | AAC | CGG | CTG | GCC | AGA | GAA | 25 |
| 1 | | Glu | His | Asn | Arg | Leu | Ala | Arg | Glu | 8 |
| 26 | CTA | AAG | AGA | CTC | AAC | CCT | CAG | TGG | GAT | 52 |
| 9 | Leu | Lys | Arg | Leu | Asn | Pro | Gln | Trp | Asp | 17 |
| 53 | GGA | GAG | AAG | CTC | TAC | CAG | GAA | GCC | CGG | 79 |
| 18 | Gly | Glu | Lys | Leu | Tyr | Gln | Glu | Ala | Arg | 26 |
| 80 | AAA | ATC | CTG | GGA | GCC | TTC | ATG | CAG | ATT | 106 |
| 27 | Lys | Ile | Leu | Gly | Ala | Phe | Met | Gln | Ile | 35 |
| 107 | ATC | ACC | TTT | AGG | GAC | TAC | CTA | CCC | ATT | 133 |
| 36 | Ile | Thr | Phe | Arg | Asp | Tyr | Leu | Pro | Ile | 44 |
| 134 | TTG | CTA | GGT | GAC | CAC | ATG | CAG | AAG | TGG | 160 |
| 45 | Leu | Leu | Gly | Asp | His | Met | Gln | Lys | Trp | 53 |
| 161 | ATA | CCC | CCA | TAT | CAA | GGC | TAC | AGT | GAA | 187 |
| 54 | Ile | Pro | Pro | Tyr | Gln | Gly | Tyr | Ser | Glu | 62 |
| 188 | TCT | GTG | GAT | CCC | AGA | ATT | TCC | AAT | GTC | 214 |
| 63 | Ser | Val | Asp | Pro | Arg | Ile | Ser | Asn | Val | 71 |
| 215 | TTC | ACC | TTC | GCC | TTC | CGC | TTT | GGC | CAC | 241 |
| 72 | Phe | Thr | Phe | Ala | Phe | Arg | Phe | Gly | His | 80 |
| 242 | TTG | GAG | GTC | CCC | TCT | AGT | ATG | TTC | CGC | 268 |
| 81 | Leu | Glu | Val | Pro | Ser | Ser | Met | Phe | Arg | 89 |
| 269 | CTG | GAT | GAG | AAT | TAT | CAG | CCA | TGG | GGG | 295 |
| 90 | Leu | Asp | Glu | Asn | Tyr | Gln | Pro | Trp | Gly | 98 |
| 296 | CCA | GAA | CCA | GAA | CTC | CCC | CTC | CAC | ACC | 322 |
| 99 | Pro | Glu | Pro | Glu | Leu | Pro | Leu | His | Thr | 107 |
| 323 | CTC | TTC | TTC | AAC | ACT | TGG | AGG | ATG | GTC | 349 |
| 108 | Leu | Phe | Phe | Asn | Thr | Trp | Arg | Met | Val | 116 |
| 350 | AAA | GAT | GGT | GGA | ATT | GAT | CCT | CTG | GTG | 376 |
| 117 | Lys | Asp | Gly | Gly | Ile | Asp | Pro | Leu | Val | 125 |
| 377 | CGG | GGC | CTG | CTG | GCC | AAG | AAA | TCC | AAG | 403 |
| 126 | Arg | Gly | Leu | Leu | Ala | Lys | Lys | Ser | Lys | 134 |
| 404 | CTG | ATG | AAA | CAG | AAT | AAA | ATG | ATG | ACT | 430 |
| 135 | Leu | Met | Lys | Gln | Asn | Lys | Met | Met | Thr | 143 |

FIG. 3-1

| | | | | | | | | | |
|---|---|---|---|---|---|---|---|---|---|
| 431 | GGA | GAG | CTG | CGC | AAC | AAG | CTT | TTC | CAG | 457 |
| 144 | Gly | Glu | Leu | Arg | Asn | Lys | Leu | Phe | Gln | 152 |
| 458 | CCA | ACT | CAC | AGG | ATC | CAT | GGC | TTT | GAC | 484 |
| 153 | Pro | Thr | His | Arg | Ile | His | Gly | Phe | Asp | 161 |
| 485 | CTG | GCT | GCC | ATC | AAC | ACA | CAG | CGT | TGC | 511 |
| 162 | Leu | Ala | Ala | Ile | Asn | Thr | Gln | Arg | Cys | 170 |
| 512 | CGG | GAC | CAT | GGG | CAA | CCT | GGG | TAC | AAT | 538 |
| 171 | Arg | Asp | His | Gly | Gln | Pro | Gly | Tyr | Asn | 179 |
| 539 | TCC | TGG | AGA | GCC | TTC | TGT | GAC | CTC | TCA | 565 |
| 180 | Ser | Trp | Arg | Ala | Phe | Cys | Asp | Leu | Ser | 188 |
| 566 | CAG | CCG | CAG | ACA | CTA | GAG | GAG | TTG | AAC | 592 |
| 189 | Gln | Pro | Gln | Thr | Leu | Glu | Glu | Leu | Asn | 197 |
| 593 | ACA | GTG | CTG | AAG | AGC | AAG | ATG | CTG | GCC | 619 |
| 198 | Thr | Val | Leu | Lys | Ser | Lys | Met | Leu | Ala | 206 |
| 620 | AAG | AAG | TTA | CTG | GGT | CTC | TAC | GGG | ACC | 646 |
| 207 | Lys | Lys | Leu | Leu | Gly | Leu | Tyr | Gly | Thr | 215 |
| 647 | CCT | GAC | AAC | ATC | GAC | ATC | TGG | ATA | GGG | 673 |
| 216 | Pro | Asp | Asn | Ile | Asp | Ile | Trp | Ile | Gly | 224 |
| 674 | GCC | ATT | GCT | GAG | CCG | CTG | GTG | GAA | AGG | 700 |
| 225 | Ala | Ile | Ala | Glu | Pro | Leu | Val | Glu | Arg | 233 |
| 701 | GGT | CGG | GTG | GGG | CCT | CTC | CTG | GCC | TGC | 727 |
| 234 | Gly | Arg | Val | Gly | Pro | Leu | Leu | Ala | Cys | 242 |
| 728 | CTC | TTG | GGC | AAG | CAG | TTC | CAG | CAG | ATC | 754 |
| 243 | Leu | Leu | Gly | Lys | Gln | Phe | Gln | Gln | Ile | 251 |
| 755 | CGT | GAT | GGA | GAC | AGG | TTC | TGG | TGG | GAA | 781 |
| 252 | Arg | Asp | Gly | Asp | Arg | Phe | Trp | Trp | Glu | 260 |
| 782 | AAC | CCT | GGG | GTC | TTC | ACG | AAC | GAG | CAG | 808 |
| 261 | Asn | Pro | Gly | Val | Phe | Thr | Asn | Glu | Gln | 269 |
| 809 | AAG | GAC | TCT | CTA | CAG | AAA | ATG | TCC | TTC | 835 |
| 270 | Lys | Asp | Ser | Leu | Gln | Lys | Met | Ser | Phe | 278 |
| 836 | TCA | CGC | CTT | GTC | TGT | GAC | AAC | ACC | CGC | 862 |
| 279 | Ser | Arg | Leu | Val | Cys | Asp | Asn | Thr | Arg | 287 |

FIG. 3-2

| | | | | | | | | | |
|---|---|---|---|---|---|---|---|---|---|
| 863 | ATC | ACC | AAG | GTC | CCA | CGG | GAC | CCA | TTC | 889 |
| 288 | Ile | Thr | Lys | Val | Pro | Arg | Asp | Pro | Phe | 296 |
| 890 | TGG | GCC | AAC | AGC | TAC | CCC | TAT | GAC | TTC | 916 |
| 297 | Trp | Ala | Asn | Ser | Tyr | Pro | Tyr | Asp | Phe | 305 |
| 917 | GTG | GAT | TGC | TCA | GCC | ATC | GAC | AAG | CTG | 943 |
| 306 | Val | Asp | Cys | Ser | Ala | Ile | Asp | Lys | Leu | 314 |
| 944 | GAC | CTG | TCA | CCC | TGG | GCC | TCA | GTG | AAG | 970 |
| 315 | Asp | Leu | Ser | Pro | Trp | Ala | Ser | Val | Lys | 323 |

| | | | | | | | | | |
|---|---|---|---|---|---|---|---|---|---|
| 971 | AAT | TAG | GGG | CCC | GCG | CTG | CAC | AGG | AAA | 997 |
| 998 | GTT | CCC | TTT | GGT | CCA | CAG | GGC | CAT | TTC | 1024 |
| 1025 | AAG | CAA | GTT | CAA | TGA | CCT | GGT | CCC | TTA | 1051 |
| 1052 | GAG | CTC | CAT | ATC | CCA | GTC | CCA | GCC | CTT | 1078 |
| 1079 | CTT | TGC | AGC | TGG | GCC | TCT | CTA | TAC | CCC | 1105 |
| 1106 | TGG | ATG | AAC | AGC | TTG | CTC | AGG | CCC | CAG | 1132 |
| 1133 | GGT | GGC | TGC | CTC | GGC | CCT | CCC | AGC | TCT | 1159 |
| 1160 | TAC | ACT | CAG | CTC | CAG | TGG | CTT | CTC | CTT | 1186 |
| 1187 | TCT | GTC | AAG | ACT | TAG | CCC | CGC | TGA | GAT | 1213 |
| 1214 | GCC | CTT | CTG | CTC | CAG | CTT | GCT | GGA | TGT | 1240 |
| 1241 | TAC | CTG | TCC | TCT | TCC | CTC | CAC | AAG | TCT | 1267 |
| 1268 | TGG | CCC | TTA | ACC | TTT | ATC | TTT | CTT | CCT | 1294 |
| 1295 | GTC | CTC | TCA | CCT | AGA | TTG | TAA | GCT | CCC | 1321 |
| 1322 | TGG | GCC | AGG | ACT | TCA | GCC | TGC | CTC | CGA | 1348 |
| 1349 | GGG | TCC | CCT | GTG | GCA | CCT | AGC | ATG | GTG | 1375 |
| 1376 | CAC | AGC | ACA | TTA | GAA | GTG | CTC | AAA | | 1399 |

—(additional sequences of non-LPO origin)

(EcoRI = cloning linker)

FIG. 3-3

RECOMBINANT PRODUCTION OF LACTOPEROXIDASE

This is a continuation of application Ser. No. 07/928,933, filed Aug. 12, 1992, now abandoned, which is a continuation-in-part of U.S. Ser. No. 07/431,634, filed Nov. 3, 1989, now abandoned, the disclosure of which is incorporated herein by reference.

TECHNICAL FIELD

The invention relates to the cloning and expression of the gene encoding mammalian lactoperoxidase. The DNAs encoding the bovine and human forms of this protein have been recovered and sequenced. The gene is also useful in the design and production of oligomeric probes, in the construction of antisense sequences that inhibit the production of lactoperoxidase, and in other aspects of oligonucleotide therapy.

BACKGROUND ART

The presence in milk and in associated secretion glands of an enzyme having peroxidase activity has been known for decades. Carlstrom, A., *Acta Chem Scand* (1969) 23:185–202, summarized the state of knowledge at that time concerning the heterogeneity of peroxidases in these sources. It was established that the peroxidase activity seemed to reside in a number of interconvertible protein or glycoprotein fractions. Subsequent investigators, for example Sievers, G., *FEBS Letters* (1981) 127:253–256, described the bovine protein as a glycosylated, single-chain protein having leucine at the N-terminus and determined the amino acid composition. The protein was shown to contain variable levels of glycosylation and to have a molecular weight of roughly 78 kd. The protein contains a heme group (protoheme IV) at its active site. Further studies of the heterogeneous forms of the bovine protein were published by Paul, K.-G., et al., *Immunol Ser* (1983) 27:15–129. Langbakk, B., et al., *FEBS* 1753 (1984) 174:300–303, showed that lactoperoxidase was present in human colostrum and disclosed a partial purification procedure for this enzyme. These authors reported that the enzyme isolated from human colostrum had stability, chromatographic and immunoreactive properties similar to that of the lactoperoxidase isolated from bovine milk.

Lactoperoxidase is a highly useful protein, as it has antimicrobial activity which permits its use as a fungicide, viricide, protozoacide and bacteriocide both in products which need preservatives and therapeutic products. In addition, because of its peroxidase activity, it can be used as a labeling and/or linking reagent in the conduct of various diagnostic and analytical assays. The production of this protein in recombinant form provides a reliable and reproducible source of this important protein.

In addition, the gene encoding lactoperoxidase or fragments thereof can be used directly in controlling the production of lactoperoxidase and in retrieving genes encoding lactoperoxidase from various sources.

DISCLOSURE OF THE INVENTION

The invention provides DNA sequences encoding mammalian lactoperoxidase enzymes and recombinant expression systems for the production of the recombinant lactoperoxidase proteins. The protein produced has wide industrial, therapeutic, and diagnostic applications in humans and in animals. In addition, the DNA sequences associated with the lactoperoxidase gene are useful in controlling the production of this protein and in diagnostic tests.

Thus, in one aspect, the invention is directed to recombinant mammalian lactoperoxidase in substantially pure form. In other aspects, the invention is directed to isolated DNA sequences encoding these proteins, to expression systems capable of producing these proteins, to recombinant host cells transformed with these expression systems, and to methods of production using these systems and cells. In addition, the invention is directed to pharmaceutical compositions containing the recombinant lactoperoxidase proteins of the invention as well as formulations suitable for diagnostic and industrial use. The invention is also directed to methods of preserving organic compositions using lactoperoxidase and to methods of treating various conditions susceptible to this enzyme.

In still other aspects, the invention is directed to the natively occurring sequence that encodes lactoperoxidase and fragments and contiguous regions thereof. These DNA molecules are useful as diagnostic probes to detect the presence or absence of genes encoding lactoperoxidase and as primers in amplification of the lactoperoxidase gene. In addition, these sequences can be used to control, either by antisense technology or by triple helix formation, the production of lactoperoxidase in living systems.

BRIEF DESCRIPTION OF THE DRAWINGS

FIG. 1 shows the complete DNA sequence encoding bovine lactoperoxidase preproenzyme and the deduced amino acid sequence.

FIG. 2 shows a comparison of the amino acid sequences of a number of mammalian peroxidases.

FIG. 3 shows the sequence of a human cDNA clone.

MODES OF CARRYING OUT THE INVENTION

As used herein, "mammalian" lactoperoxidase refers to a protein having peroxidase activity, as assayed by standard enzymological tests, and which protein is present in the secretions of milk-secreting glands and in the glands themselves. Such conventional tests for peroxidase activity are commercially available and described in standard references such as *Methods in Enzymology*. Illustrative of such proteins are the bovine protein having the amino acid sequence shown in FIG. 1 and the related human sequence. However, also included are such proteins encoded by allelic variants of the DNA sequence there shown, as well as those encoded by any other members of a gene family which provides these milk-related proteins and those of other mammalian species.

Also included in the group of lactoperoxidases of the invention are modified forms of these mammalian lactoperoxidases which result from noninterfering deletions, substitutions, or alterations of the amino acid sequence. Also included are fragments of these sequences which retain peroxidase activity. In general, these modified forms of mammalian lactoperoxidases will be at least 80%, preferably 90%, and more preferably 95% homologous with at least one member of the mammalian lactoperoxidase family.

By "purified" is meant that the lactoperoxidases of the invention are free from association with proteins and other materials in the presence of which they normally occur. As the claimed proteins are recombinantly produced, there are no traces of such associated materials in the mammalian proteins typically purified from these recombinant sources.

"Operably linked" refers to a juxtaposition wherein the components are configured so as perform their usual functions; thus, control sequences or promoters operably linked to a coding sequence are capable of effecting the expression of the coding sequence.

"Control sequence" refers to a DNA sequence or sequences which are capable, when properly ligated to a desired coding sequence, of effecting its expression in hosts compatible with such sequence. These sequences include at least promoters, both in procaryotic and eucaryotic hosts, and, optionally, transcription termination signals. Additional sequences which may be required or helpful in effecting expression may also be identified and incorporated. As used herein, "control sequences" refers to whatever DNA sequence may be required to effect expression of the operably linked coding sequence in the particular host used.

"Cells" or "cell cultures" or "host cells" are often used interchangeably, as will be clear from the context. These terms include the immediate subject cell, and, of course, the progeny thereof. It is understood that not all progeny are exactly identical to the parental cell due to chance mutation or differences in environment, but such altered progeny are included in these terms as long as they retain the characteristics relevant to those confirmed on an originally transformed cell. In the present case, for example, the included progeny would be those which retain an expression system capable of effecting the production of the desired lactoperoxidase.

The DNA sequences encoding the illustrative bovine and human lactoperoxidases of the invention were obtained from cDNA libraries obtained from bovine and human milk glands. In the case of these illustrative proteins, bovine lactoperoxidase (LPO) was purified from commercial preparations of lactoperoxidase, and internal amino acid sequence information was obtained from CNBr fragments of the purified material. Probes designed from these determined sequences were used to screen a cDNA library from bovine milk gland and three clones were obtained which encoded the bovine LPO sequence shown in FIG. 1. The sequence contains 712 amino acids, including the signal sequence and pro sequence. Two putative signal peptidase cleavage sites (1 and 2) and two possible alternative termini of the cleaved propeptide (A and B) are indicated on the figure. Thus the mature protein may begin at the Asp at 101 or the Leu at 129.

Genomic DNA was also prepared from a bovine library and the retrieved bLPO sequence used to perform Southern blots on SDS gels of the genomic bank. The results of these Southern blots indicated that multiple genes may encode bovine lactoperoxidase proteins; however, the multiple bands found may also be attributable to related peroxidases.

The bovine clone was also used to screen a human mammary tissue cDNA library, and a clone encoding the carboxy-terminal 324 residues of human cDNA for LPO was isolated. The human sequence shown in FIG. 3 was found to be highly homologous to the bovine protein.

The illustrated bovine and human sequences permit the retrieval of the corresponding LPO-encoding genes from cDNA or genomic libraries prepared from other mammalian species. As high homology is expected between these species, stringent conditions can be used, thus eliminating false positives. Examples of stringent conditions include hybridization at 4×SSC at 65° C. followed by one hour washing in 0.1×SSC at 65° C., or hybridization in 50% formamide, 4×SSC, at 42° C. followed by washing in 0.1×SSC at 65° C. for an hour.

Thus, as the bovine sequence is available, a cDNA or genomic DNA encoding lactoperoxidases present in other mammalian sources can also be recovered either from genomic or cDNA banks using this sequence as a probe. Hybridization under high stringency with the DNA of FIG. 1 is possible due to the homology of the lactoperoxidases in mammals. In addition, lactoperoxidases may be recovered from cDNA libraries prepared from mammary glands by hybridization under stringent conditions to DNA probes which simply encode the amino acid sequence shown in FIG. 1—i.e., may be degenerate, due to the redundancy of the code, with the cDNA sequence there shown.

The lactoperoxidase-encoding DNA sequences may include those having nucleotide sequences corresponding to those that occur natively in various mammalian subjects or may be degenerate forms thereof when used in expression systems for production of the protein. However, for use as probes or in the control of the production of lactoperoxidase as generated in native systems, or as primers for the retrieval of lactoperoxidase genes, the relevant sequences must conform, at least reasonably closely, to the natural sequences of nucleotides since their capacity in these utilities depends on hybridization or other binding to the native materials in a sequence-specific manner. Thus, the relevant DNAs or other oligomers should be at least 90% homologous, preferably 95% homologous, and most preferably 99% or completely homologous to the natively occurring corresponding sequences. However, for use in the control of production of recombinant lactoperoxidase, the oligomers should be correspondingly homologous to whatever construct is employed in the recombinant production host. If contiguous regions of the lactoperoxidase gene, such as termination sequences or leader sequences are employed for the control of lactoperoxidase production in native context, these, too, should be homologous, as described, to the native forms of these contiguous regions.

When used as diagnostics, the lactoperoxidase-encoding or contiguous oligomers of the invention may optionally be labelled using conventional labels such as enzyme, fluorescent, or radiolabels.

Included within the invention are lactoperoxidases from mammalian cells which are characterized by: 1) the combination of peroxidase activity with encoding by a DNA sequence which hybridizes under stringent conditions to the cDNA encoding the bovine lactoperoxidase exemplified in FIG. 1 herein; or 2) the combination of peroxidase activity, encoding by a DNA which hybridizes under stringent conditions to a DNA which encodes the illustrated bovine lactoperoxidase of FIG. 1, and origin of said DNA in the reverse transcripts of mRNA from milk-secreting gland cells; or 3) proteins which retain peroxidase activity and are at least 80% homologous, and preferably 90% homologous, and most preferably 95% homologous, to the proteins which are classified as lactoperoxidases by the foregoing definitions.

As will be clear from the foregoing, DNA segments "related to" the DNA encoding lactoperoxidase include those DNA molecules whose sequence is designed on the basis of the coding sequence and/or contiguous regions in the message and/or contiguous control regions characteristic of the gene. The design of the sequence follows generally understood rules of duplex hybridization and triplex formation. As will be evident to those of ordinary skill, for certain utilities, modified backbone linkages can be included in the DNA molecule. However, for other applications such as gene therapy, it is preferred that the native phosphodiester linkage be employed.

UTILITY AND ADMINISTRATION

The lactoperoxidases of the invention are useful, in one aspect, as antimicrobial agents both in therapeutic contexts and to preserve a variety of perishable goods. The lactoperoxidases of the invention are capable of killing fungi, viruses, protozoa and bacteria, and are effective agents against infectious diseases as well as disorders of the immune system such as malignancies, autoimmune disease, and transplant rejections.

For therapeutic purposes, the lactoperoxidase of the invention is formulated according to standard procedures for the formulation of proteinaceous active ingredients, a review of which is found in *Remington's Pharmaceutical Sciences*, Mack Publishing Company, Easton, Pa., latest edition. The therapeutic compositions are administered, preferably, systemically, most commonly by injection, either intravenously, intramuscularly, subcutaneously, or intraperitoneally. Formulations for injection are generally aqueous solutions or suspensions in physiologically compatible buffers such as Hank's solution or Ringer's solution. In addition, the protein may be formulated as a solid, for example, by lyophilization, and then reconstituted in suitable liquid for administration to the subject.

In addition, systemic administration may be achieved by transdermal or transmucosal administration using a membrane penetrant such as bile salts or fusidic acids and their analogs. Suitable pharmaceutically acceptable nontoxic detergents may also be used. The administration across membranes can be effected at vulnerable locations, especially, such as through nasal sprays or suppositories.

Although it is more challenging to do so, the proteins of the invention may also be administered orally when properly formulated to protect them from digestion.

In addition, it has lately been possible to administer proteins through in situ production thereof as a result of expression of a gene transformed into the subject. Thus, an alternate route of administration is through gene therapy to obtain a transgenic subject.

In addition, the lactoperoxidases of the invention may be administered locally to counteract, for example, localized infection or malignancy. Such local administration may be topical in the form of ointments, creams, salves, or gels, or may be by a transdermal patch containing a limited amount of drug, or by local subcutaneous injection.

The dosage and route of administration are highly dependent on the nature of the subject, the nature of the conditions being treated, and the judgment of the physician or veterinarian. However, suitable dosage ranges for treatment of infectious diseases are of the order of 0.01–100 mg/kg/day.

In addition to use as therapeutic agents, the proteins of the invention can be used to stabilize perishable goods such as foods, beverages, cosmetics, and the like. For use in these applications, the protein can be added to the material in an amount of 0.01–5%, typically.

Finally, the lactoperoxidases of the invention may also be used as labeling reagents for immunoassays or other specific binding assays. In these applications, the enzyme is conjugated to a component of the test system designed to identify the analyte characteristic of, for example, a disease condition. Applications in ELISA assays, for example, are analogous to the use of horseradish peroxidase in these systems.

DNA encoding mammalian lactoperoxidase or DNA representing contiguous regions of the lactoperoxidase gene in mammalian species are also useful in a variety of contexts. In addition to the utility of the lactoperoxidase-encoding DNA, including the various degenerate forms thereof, in the recombinant production of the protein, the DNA molecules themselves are useful in a variety of diagnostics and other biological contexts. For such use, the oligomers may be the antisense forms of the coding or contiguous regions as found in the native gene, may be constructed so as to hybridize to the duplex forms of the native gene and its contiguous regions and/or may contain modified internucleotide linkages such as phosphorothioate linkages, phosphoramidate linkages, methylphosphonate linkages, and the like as is generally known in the art. In addition, modifications to the sugar moieties and base residues that do not interfere with sequence-specific hybridization may also be included.

These forms of mammalian lactoperoxidase DNA are useful in assay systems designed to detect the presence or absence of lactoperoxidase-related genomic material by providing these DNA molecules or fragments thereof under conditions wherein complexes are formed with the target lactoperoxidase-related DNA. The detection of the complexes is then effected by generally available art-known means, such as detection of complexed forms of nucleotides through specific antibodies, labeling of the DNA molecules of the invention with radiolabel, fluorescent label or other label such as enzyme label and the like. These fragments may also be used as primers for conduct of the polymerase chain reaction to amplify the lactoperoxidase gene, including, if desired, its surrounding control sequences or portions thereof. The lactoperoxidase-related DNA of the invention may also be used to control the production of lactoperoxidase through an antisense mechanism, utilizing the antisense form of the native sequence or by triple helix formation with duplex DNA associated with the lactoperoxidase gene. Control of such production may be especially useful in the case of recombinant production of the protein since these methods can be used to diminish the level of lactoperoxidase production during the early phases of host cell growth and then removed when production is desired.

Finally, the lactoperoxidase encoding DNA and associated control fragments can be used in gene therapy to replace defective portions of the lactoperoxidase gene in cells deficient in this production.

Retrieval of the Bovine Lactoperoxidase Gene

A cDNA library is prepared from milk gland cells of bovine teats using standard procedures, as follows: A preparation of mRNA is obtained from these cells using standard extraction and oligo-dT chromatographic techniques. The cDNA library is then prepared, for example, using the lambda-gt10/lambda-gt11 vectors of Huynh, V. T., et al., *DNA Cloning Techniques: A Practical Approach* (IRL Press, Oxford, 1984). In the present work, the commercially available lambda-ZAP-II vector from Stratagene, San Diego, Calif., was employed using the manufacturer's instructions.

This library is then screened with probes designed to correspond to the sequence obtained from isolated bovine lactoperoxidase protein. The bovine lactoperoxidase is purified from commercially available proteins using an HPLC column and recovering a single peak.

The recovered protein is then hydrolyzed using CNBr, and the fragments are sequenced. A set of oligonucleotide probes is then designed on the basis of two sequences obtained in the full-length protein.

The library from bovine teats was probed using the two kinased oligomers, and three clones were recovered which hybridized to both. The screening was done under standard, moderately stringent conditions. All three retrieved clones contained portions of the open reading frame shown in FIG. 1 encoding 712 amino acids, and one clone contained the complete sequence shown in FIG. 1. This clone was designated pIDNbLPO-1 and was deposited at the American Type Culture Collection. Rockville, Md., on Nov. 2, 1989 under the conditions of the Budapest Treaty. ATCC accession no. 68162. The mature protein begins at the aspartic acid residue shown in position 101. Since lactoperoxidase is a secreted protein, the upstream portions contain both a signal and a pro-LPO sequence. A human clone, pIDNhLPO-3, with the sequence shown in FIG. 3, was also deposited Nov 2, 1989 at the ATCC under the conditions of the Budapest Treaty and has ATCC accession no. 68163.

The resulting clone is then ligated into suitable expression systems and transformed into host cells for production of the protein. The LPO can be produced as an intracellular protein by removal of the DNA sequence encoding the leader and pro sequence and inserting at ATG start codon upstream of the N-terminal aspartic acid residue. Alternatively, the heterologous or homologous signal sequences can be used to effect the secretion of the protein.

Construction of expression systems operable in a spectrum of host cells is well within ordinary skill. The retrieved cDNA or synthetic or partially synthetic DNA encoding the desired protein is ligated to control sequences appropriate to the intended host. The coding sequence ligated to appropriate controls can be included on a self-replicating vector, as is ordinarily the case when yeast or procaryotic hosts are used, or may be designed to integrate into the host cells' chromosome, as is often the case for mammalian cell hosts.

For procaryotic expression, suitable promoters include the regulatable trp promoter, the regulatable lac promoter, or the commercially available hybrid of these systems, variously designated the trc or tac promoter. Signal sequences operable in bacteria are available from the penicillinase gene, which can also be used with its own promoter. Typical replicating vectors suitable for transformation of *E. coli*, for example, include the pBR322 derived vectors and vectors related to the pUC series. However, other bacterial hosts with suitable modifications of the control systems in vectors can also be used, including, for example. *Bacillus subtilis* various pseudomonas, and related host strains. However, expression in *E. coli* is generally the most convenient.

Yeasts are also commonly used as eukaryotic hosts, and a number of promoters, especially those which are indigenous as promoters for synthesis of the glycolytic enzymes, such as the 3-phosphoglycerate kinase (PGK) promoter, the enolase promoter, or the promoter associated with the Leu2 gene can be used. Signal sequences which are operable in yeast include those derived from the alpha-factor gene. Yeast vectors commonly include a replication site, such as the two-micron replicon.

Suitable mammalian expression systems generally comprise viral promoters such as the SV40, polyoma, adenovirus, bovine papilloma virus (BPV), or avian sarcoma virus promoters. However, also useful in mammalian systems are indigenous promoters such as the regulatable metallothionein promoter. Additional controls are generally desirable in mammalian systems including terminating sequences for transcription and various enhancers. Signal sequences applicable to mammalian systems include those associated with normally-secreted mammalian proteins such as the various growth hormones and insulin.

In addition, although less convenient, plant cells can also be used as hosts using appropriate controls such as nopaline synthetase promoter. A commonly used system for production of recombinant proteins includes the baculovirus/insect host system.

Additional features may be included in the expression systems such as, for example, in mammalian systems, amplification by cotransformation with an amplifiable gene such as that encoding dihydrofolic reductase (DHFR).

Depending on the nature of the expression system chosen, the desired lactoperoxidase is recovered and purified from the recombinantly transformed host. The host cell is cultured under conditions favorable for the expression of the lactoperoxidase gene—e.g., in prokaryotic systems, if expression is under control of the trp promoter, diminished concentrations of tryptophan or the presence of a tryptophan inhibitor, such as indoleacetic acid; in mammalian systems where the lactoperoxidase gene may be under control of the metallothionein system, in the presence of metal ions capable of inducing this promoter.

If the lactoperoxidase is produced as intracellular protein, the cells are lysed, and the lactoperoxidase separated from the cellular proteins. In general, it is more convenient to produce the lactoperoxidase as a secreted protein and to recover it from the medium as the levels of contaminating proteins are lower.

Standard purification procedures are employed such as ion exchange chromatography, affinity chromatography, differential centrifugation, ammonium sulfate precipitation, gel filtration and the like.

Preparation of Antibodies

The purified recombinant lactoperoxidase of the invention can be used to induce the formation of antibodies specifically immunoreactive with this protein. Antibodies are raised using conventional immunization protocols in suitable responsive hosts such as rabbits or mice. The high titer polyclonal antiserum can then be retrieved, or peripheral blood lymphocytes or spleen cells immortalized using standard techniques to obtain immortalized cells capable of secreting monoclonal antibodies immunoreactive with lactoperoxidase.

We claim:

1. An expression system which, when contained in a recombinant host cell, expresses a DNA sequence encoding a human or bovine lactoperoxidase, wherein said expression system comprises (a) the DNA sequence as shown in FIG. 1 or 3 operably linked to (b) control sequences compatible with said host cell whereby said DNA is expressed in said host cell.

2. A recombinant host cell which contains the expression system of claim 1.

3. A method to produce lactoperoxidase which method comprises culturing the recombinant host cells of claim 2 under conditions suitable to effect the expression of DNA encoding said lactoperoxidase and recovering the lactoperoxidase produced.

4. A DNA molecule comprising the nucleotide sequence shown in FIG. 1 or 3 in isolated and purified form.

5. A DNA molecule in isolated and purified form that is the sense or antisense strand of the DNA sequence as shown in FIG. 1 or 3.

6. The DNA molecule of claim 5 which is labeled.

7. A DNA sequence encoding bovine lactoperoxidase, said DNA comprising the sequence:

ATGTGGGT CTGTCTCCAA CTTCCAGTCT TTTTG-
GCTTC CGTGACCTTA TTCGAGGTTG CAG-
CATCTGA CACAATTGCA CAGGCCGCCA GCAC-
CACCAC CATCTCTGAT GCTGTGAGTA
AGGTCAAGAT CCAGGTCAAC AAGGCCTTCC
TGGATTCCCG GACCAGGCTG AAGACGACCT
TGAGCTCTGA GGCACCCACC ACCCAACAGC
TCTCAGAGTA CTTCAAGCAC GCAAAGGGCC

GGACCCGCAC GGCCATTCGC AACGGGCAGG
TGTGGGAGGA GTCCTTAAAG AGGCTGAGGC
GGGACACAAC CCTGACCAAC GTCACAGACC
CTAGCCTGGA CTTGACTGCA CTCTCCTGGG
AGGTGGGCTG CGGTGCCCCG GTTCCTCTGG
TGAAATGTGA TGAAAACAGC CCTTACCGCA
CCATCACGOG AGACTGTAAT AACAGGAGGA
GCCCCGCACT GGGCGCCGCC AACAGGGCGC
TGGCGCGCTG GCTGCCGGCG GAGTACGAGG
ACGGGCTCGC CCTGCCCTTC GGCTGGACGC
ACAGGAAGAC GCGCAACGGC TTCCGCGTCC
CGCTGGCCCG GGAGGTATCC AACAAAATTG
TAGGCTACCT GGACGAAGAG GGTGTTCTGG
ACCAAAACAG GTCCCTGCTC TTCATGCAGT
GGGGTCAGAT TGTGGACCAC GACCTGGACT
TCGCCCCGGA AACGGAACTG GGGAGCAACG
AGCACTCTAA AACCCAGTGT GAGGAGTACT
GTATCCAGGG AGACAACTGC TTCCCCATCA
TGTTGCCGAA AAATGATCCC AAGTTGAAGA
CTCAAGGGAA ATOCATGCCT TTCTTCCGAG
CCGGGTTTGT CTGCCCCACT CCACCTTACC
AGTCGTTGGC CCGAGAACAG ATCAATGCTG
TGACCTCCTT CCTGGACGCC AGCTTAGTGT
ACGGCTCTGA GCCCAGTCTG GCCAGCCGTC
TCCGGAACCT CAGCAGCCCG CTGGGCCTCA
TGGCTGTCAA CCAAGAAGCC TGGGACCACG
GGCTGGCCTA CCTGCCCTTT AACAACAAGA
AGCCGAGCCC CTGTGAGTTC ATCAACACCA
CCGCCCGCGT GCCCTGTTTC CTGGCGGGAG
ATTTTCGAGC CTCAGAGCAG ATTCTGCTGG
CCACTGCCCA CACCCTCCTT CTCCGGGAGC
ACAACCGGCT CGCCAGAGAA CTAAAGAAAC
TCAACCCTCA CTGGAATGGA GAGAAGCTCT
ACCAGGAAGC CCGGAAAATC CTGGGAGCCT
TCATACAGAT CATCACCTTT AGGGACTACC
TACCCATTGT GCTAGGTAGT GAGATGCAGA
AGTGGATCCC GCCCTACCAA GGCTATAATA
ACTCTGTGGA TCCCCGAATT TCCAATGTCT
TCACCTTTGC CTTCCGCTTT GGCCACATGG
AGGTTCCCTC CACTGTGTCC CGCCTGGATG
AGAATTACCA GCCATGGGGT CCGGAAGCAG
AGCTCCCCCT ACACACCCTC TTCTTCAACA
CCTGGAGGAT AATCAAAGAC GGTGGAATTG
ACCCTCTGGT GCGGGGTCTG CTGGCCAAGA
AGTCCAAACT GATGAATCAG GATAAAATGG
TGACGAGTGA GCTGCGCAAC AAGCTTTTCC
AGCCCACTCA CAAGATCCAC GGCTTTGACC
TGGCTGCTAT CAACTTACAG CGTTGCCGAG
ACCATGGGAT GCCTGGGTAC AACTCCTGGA
GGGGCTTCTG TGGCCTCTCA CAGCCCAAGA

CACTGAAGGG GCTGCAGACT GTGCTGAAGA
ACAAGATACT GGCTAAGAAG TTAATGGATC
TCTATAAGAC CCCCGACAAC ATTGACATCT
GGATTGGAGG CAACGCTGAG CCCATGGTAG
AAAGGGGCCG GGTGGGGCCA CTCCTGGCCT
GCCTCCTAGG GAGGCAATTC CAGCAGATAC
GTGATGGGGA CAGGTTCTGG TGGGAGAACC
CTGGGGTCTT CACTGAGAAG CAGCGGGACT
CTCTACAGAA AGTGTCCTTC TCACGCCTCA
TCTGTGACAA CACCCACATC ACGAAGGTCC
CGCTGCATGC CTTCCAGGCC AACAACTACC
CACATGACTT TGTGGATTGC TCAACCGTTG
ATAAGCTGGA TCTCTCACCC TGGGCCTCCA
GGGAGAAT.

8. A DNA sequexce encoding the carboxy terminus of human lactoperoxidase, said DNA comprising the sequence:
GGAGCATAAC CGGCTGGCCA GAGAACTAA
GAGACTCAAC CCTCAGTGGG ATGGAGAGAA
GCTCTACCAG GAAGCCCGGA AAATCCTGGG AGC-
CTTCATG CAGATTATCA CCTTTAGGGA CTAC-
CTACCC ATTTTGCTAG GTGACCACAT GCA-
GAAGTGG ATACCCCAT ATCAAGGCTA
CAGTGAATCT GTGGATCCCA GAATTTCCAA TGTCT-
TCACC TTCGCCTTCC GCTTTGGCCA CTTGGAGGTC
CCCTCTAGTA TGTTCCGCCT GGATGAGAAT TAT-
CAGCCAT GGGGGCCAGA ACCAGAACTC CCCCTC-
CACA CCCTCTTCTT CAACACTTGG AGGATGGTCA
AAGATGGTGG AATTGATCCT CTGGTGCGGG GCCT-
GCTGGC CAAGAAATCC AAGCTGATGA AACA-
GAATAA AATGATGACT GGAGAGCTGC GCAA-
CAAGCT TTTCCAGCCA ACTCACAGGA
TCCATGGCTT TGACCTGGCT GCCATCAACA
CACAGCGTTG CCGGGACCAT GGGCAACCTG
GGTACAATTC CTGGAGAGCC TTCTGTGACC TCT-
CACAGCC GCAGACACTA GAGGAGTTGA ACA-
CAGTGCT GAAGAGCAAG ATGCTGGCCA AGAAGT-
TACT GGGTCTCTAC GGGACCCCTG ACAACATCGA
CATCTGGATA GGGGCCATTG CTGAGCCGCT GGTG-
GAAAGG GGTCGGGTGG GGCCTCTCCT GGCCTGC-
CTC TTGGGCAAGC AGTTCCAGCA GATCCGTGAT
GGAGACAGGT TCTGGTGGGA AAACCCTGGG
GTCTTCACGA ACGAGCAGAA GGACTCTCTA
CAGAAAATGT CCTTCTCACG CCTTGTCTGT
GACAACACCC GCATCACCAA GGTCCCACGG GAC-
CCATTCT GGGCCAACAG CTACCCCTAT GACT-
TCGTGG ATTGCTCAGC CATCGACAAG CTGGAC-
CTGT CACCCTGGGC CTCAGTGAAG.

* * * * *